United States Patent
Smith

Patent Number: 6,010,467
Date of Patent: Jan. 4, 2000

[54] BACK TRIGGER-POINT INSTRUMENT

[75] Inventor: William A. Smith, New Paltz, N.Y.

[73] Assignee: William Arthur Smith, New Paltz, N.Y.

[21] Appl. No.: 08/916,513

[22] Filed: Aug. 22, 1997

[51] Int. Cl.⁷ .............................. A61H 39/04; A61N 1/32
[52] U.S. Cl. .............................. 601/15; 601/17; 601/135; 607/115; 607/145; 607/46
[58] Field of Search .................. 601/15, 17, 20, 601/21, 80, 135, 137, 138, 70, 46, 67; 607/3, 44, 46, 145, 148–51, 153, 115, 79; 606/204; 600/384

[56] References Cited

U.S. PATENT DOCUMENTS

| | | |
|---|---|---|
| 1,612,343 | 12/1926 | Amussen . |
| 1,740,240 | 12/1929 | Honey . |
| 1,812,224 | 6/1931 | Treibmann . |
| 3,219,029 | 11/1965 | Richards et al. ........................ 128/24.5 |

FOREIGN PATENT DOCUMENTS

| | | | |
|---|---|---|---|
| 102325 | 11/1937 | Australia .............................. 607/150 |
| 2563437 | 10/1985 | France ..................................... 601/17 |
| 886218 | 2/1953 | Germany ............................... 607/145 |
| 2751-130 | 5/1979 | Germany ............................... 607/151 |
| 42550 | 5/1917 | Sweden ................................... 601/21 |

*Primary Examiner*—Danton D. DeMille
*Attorney, Agent, or Firm*—Joseph B Taphorn

[57] ABSTRACT

An apparatus for enabling the patient himself or herself to engage the skin on his or her back to locate and treat trigger points thereunder, using a source of pulsed voltage. The apparatus includes a wand having a generally rigid and electrically-conductive arcuate handle of about an arm's length or less in length, a spade-shaped electrically-conductive extension with a free end formed with tapering straight edges merging in a rounded point and welded on its other end to the handle, and a cable secured on the other end of the handle to connect to connect the extension electrically to the source of pulsed voltage. A somewhat comparably-shaped sponge is fixed to the extension. A grip at the other end of the handle facilitates moving the wand so that a tapering straight edge and/or the rounded point of the spade-shaped extension glides over the back's skin when searching for trigger points, and for holding the rounded point there when a trigger point is located to enable precise electrically stimulation of the tissue near the trigger point.

13 Claims, 1 Drawing Sheet

BACK TRIGGER-POINT INSTRUMENT

FIELD OF THE INVENTION

This invention relates to "trigger point" therapy, and more particularly to an instrument and system for enabling an individual himself or herself to utilize modern electrical trigger-point therapy to alleviate associated tissue pain.

BACKGROUND OF THE INVENTION

"Trigger Points"

Trigger points are very real entities that have a definite physiological manifestation. They are often but not exclusively palpable as tiny nodules in and near muscle, in areas of muscle tightness ("taut bands"). They are also detectable with electrical devices ranging from electrodes placed on the skin, to needle electromyography. But they are difficult or impossible to detect in biopsy.

Trigger points are often associated with muscular pain in adjacent, and sometimes remote, areas. Resolving the trigger point will often alleviate the associated pain. This is usually done either through direct pressure on the trigger point, or mechanically by contacting the trigger point with a fine needle, or through electrical stimulation or pharmacological means such as direct injection of local anesthetics. Thus the discovery and resolution of trigger points is often a goal of therapy for muscular-skeletal pain.

There are other kinds of "points" as well. For example, there are "tender points", "acupressure points" and "acupuncture points" from traditional Chinese medicine, and "polarity points". These are distinct from "trigger points".

The underlying physiology of trigger points is not necessarily fully understood. The best explanation may be that trigger points are caused by intrafusal contractions (localized muscle contractions) caused by a sympathetic nervous system. The physiological function that trigger points serve has not been positively determined.

In summary, trigger points are small (a few millimeters or less) nodules within a tight band of muscle that are tender to the touch and cause a characteristic pattern of pain, tingling, or numbness when subjected to sustained pressure. They have also been documented in skin, ligament, tendon, scar and breast tissue and periostenen. The trigger point is often associated with referred pain, usually locally (in the same muscle), but sometimes surprisingly remote. Inactivation of the trigger point reduces or resolves the associated pain.

Discovery and Resolution through Electrical Stimulation

Resolving the trigger point will often alleviate the associated pain. This may be done through myofascial electrical stimulation of the trigger point. An electrical wand or probe (an electrode) is moved over the skin in the suspect area for the trigger point. When the precise area for the trigger point is discovered, a ripple effect or a tingling sensation may be felt in the associated muscle which when continued for a while alleviates the associated pain and resolves the trigger point in a few, if not one, treatment(s) of several minutes each. The electrical stimulation relaxes muscle spasms and increases localized circulation to fix the source of the trigger point.

The wand, more or less in the shape of a pencil or flashlight, is formed at one end with a thin, flat, spatula-like or rectangular, flat blade extension, the outer edge of which is run over a patient's skin to discover the trigger point causing the pain. Sometimes an outer corner of the extension is utilized to locate more precisely the trigger point and apply even more localized electrical stimulation. Efforts to improve the electrical connection between the extension and the patient's skin have included coating the extension with a conductive gel.

Machine for Source of Electrical Stimulation

A machine for the source of electrical stimulation of trigger points, is manufactured by the Rich-Mar Corporation; Rt. 2, Box 879; Inola, Okla. 74036-0879; as Model HV 2000, a high voltage pulsed Current (HVPC) device. It provides a suitable pulsed high voltage at an appropriate frequency and micro-amperage to the probe or wand. The wand, more or less in the shape of a pencil or flashlight, is used by therapists to locate precisely and treat the trigger points. This works fine in the hands of a therapist, but a pencil- or flashlight shaped wand is ill suited for an individual to move across his back to locate precisely therein a trigger point and to thereafter hold the wand in place and continuously apply electrical stimulation to the trigger point.

SUMMARY OF THE INVENTION

Accordingly, it is an object of the invention to provide an instrument which will enable an individual himself or herself to discover and to treat trigger points located on his back.

A more particular object of the invention is to provide a specially-shaped instrument which can function as an electrical wand in association with a machine such as the Rich-Marr Model HV 2200 mentioned above, and enable an individual himself or herself to discover and to treat trigger points located on his back.

Another object of the invention is to provide such a specially-shaped electrical wand which is simple and easy to use.

Yet another object of the invention is to provide such a specially-shaped electrical wand which is inexpensive of construction and easy of manufacture.

The objects of the invention are achieved through the use of an arcuate wand or probe which is formed at one end with an electrically-conductive spade-like extension having a rounded point on its free end and bearing on its free end a sponge which may be soaked in water by the patient just before use. Preferrably the rounded point on the free end of the extension is formed at the juncture of two tapering straight edges. After wetting the sponge, the patient grasps the other end of the arcuate wand with one or both hands and positions its spade-like-extension free end over a suspected trigger point area on his or her back so that one of its tapering straight edges or rounded point touches the associated skin. He or she then slides the straight edge or rounded point of the spade-like extension back and forth over the skin of the suspected area until the trigger point is discovered, and then places the point there for several minutes. The wet sponge will enhance the electrical conductivity between the arcuate-wand spade-like extension and the skin overlying the trigger point area.

An advantage of the invention is that the patient can utilize the procedure whenever a tissue pain arises. No longer must he or she await the availability of a physical therapist to alleviate the pain.

A feature of the invention is that the patient can apply the electrical stimulation as long as it seems beneficial. No longer is the patient's treatment dependent on the time slot available to him in the physical therapist's office.

BRIEF DESCRIPTION OF THE DRAWINGS OF A PREFERRED EMBODIMENT

These and other objects, features and advantages of the invention will become apparent from a reading of the following description of a preferred embodiment of the invention when considered with the accompanying drawings wherein.

DETAILED DESCRIPTION OF A PREFERRED EMBODIMENT

Figure 1:
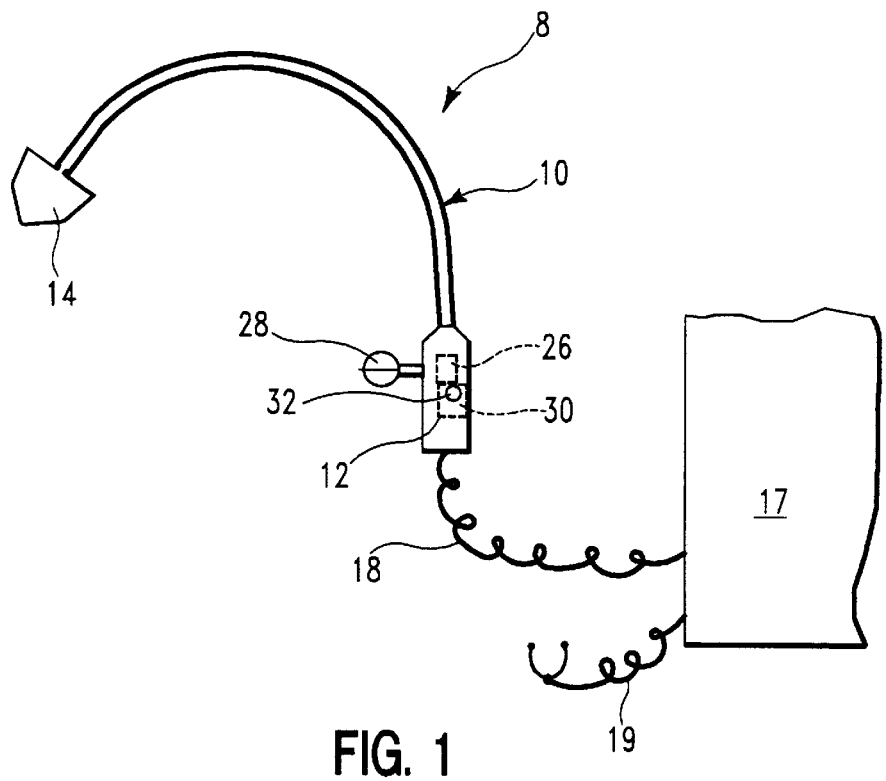
FIG. 1 is a diagrammatic view in perspective of a system embodying the invention.
Figure 2:
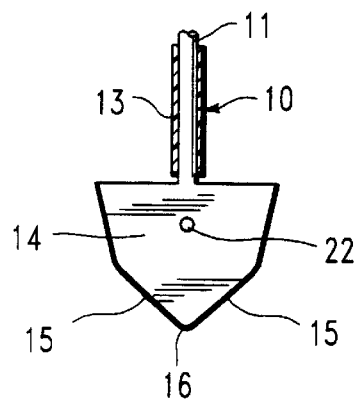
FIG. 2 is an enlarged front view of the wand spade-like extension of FIG. 1.
Figure 3:
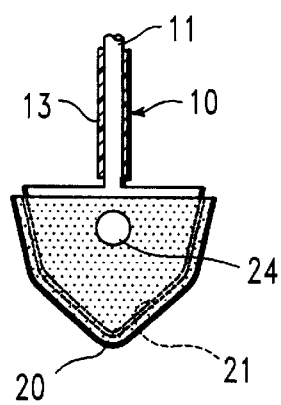
FIG. 3 is a another view of the spade-like extension of FIG. 2 but bearing a sponge.
Figure 4:
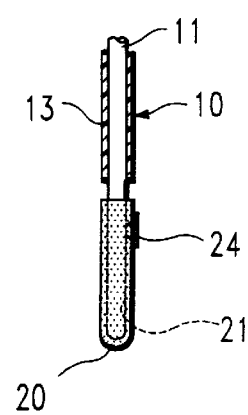
FIG. 4 is a left-hand side view of the sponge-covered spade-like extension of FIG. 3.

Referring now more particularly to FIG. 1 of the drawings, the wand or probe, generally indicated by the numeral 8, is shown as being in the shape of an arcuate handle or bow generally indicated by the numeral 10. The handle or bow 10 may be an arm's length or less in length. Its curve allows one to readily reach behind one's back to engage the skin thereon. It is preferrably made of a rigid electrically-conductive rod 11 (FIGS. 2–4) of a material such as stainless steel, and covered with a suitable insulating plastic 13. One end of the handle 10 may mount an electrically-insulating grip 12 for facilitating moving the wand 8.

The other end of the handle 10 mounts an electrically-conductive, flat and thin spade-like extension 14 of stainless steel or the like. The spade-like extension 14 is attached to the stainless steel rod 11 of the handle 10 as by welding. The spade 14 is formed at its free end with tapering straight edges 15 which meet in a rounded point 16.

The spade 14, via the stainless steel rod 11, is electrically connected to a suitable source 17 of pulsed voltage, e.g. the Rich-Mar Model HV 2000 mentioned above, through a suitably insulated electrical cable 18. A cable 19 extending from the source 17, and having a spring clamp at the free end of it, completes the circuit for the electric current to follow.

Attached to the spade-like extension 14 is a sponge 20. The sponge 20 is generally shaped like the spade-like extension 14. It is formed with an internal pocket 21 (FIGS. 3 and 4)) so as to be received on the free end of the spade-like extension 14. It may be secured thereon by a snap consisting of male device 22 (FIG. 2) formed on the surface of the extension 14 and a coacting female device 24 (FIGS. 3 and 4) mounted on the sponge 20. A moist sponge 20 enhances the electrical connection of the spade-like extension 14 with the patient's skin in the area of the trigger point.

The grip 12 may mount internally a rheostat 26 in circuit with the cable 18, which rheostat may be adjusted by rotating an external knob 28 on the grip 12 to regulate further the current applied by the spade-like extension 14.

The grip 12 may also mount internally in circuit with the cable 18, an on/off switch 30 controlled by an external push button 32, to cut off the power applied to the spade-like extension 14 independently of a control switch (not shown) on the electrical source 17.

In use, the patient would grasp the wand handle 10 as by its grip 12, and connect the electrical cord 18 to the source 17 of pulsed voltage if not already so connected. Next he or she would dip the sponge 20 into some water to moisten it. Then, after moving the grip on/off switch button 32, the patient would move a straight edge 15 or rounded point 16 or the spade 14 to the pain-affected area of his or her back to endeavor to locate the trigger point. Then he or she would place the rounded point 16 over the the trigger point, and experience a ripple effect or tingling sensation in the associated muscle or other affected tissue. The electrical stimulation shortly alleviates the associated pain and resolves the trigger point in a few, if not one, treatment(s) of several minutes each.

The insulated nature of the handle 10 prevents the application of unwanted electrical stimulation elsewhere.

While there has been described a preferred embodiment of the invention, it will be apparent to those skilled in the art that other embodiments utilizing the principles of the invention may be readily created. It is therefore intended to be limited only by the spirit or scope of the appended claims.

What is claimed is:

1. A wand for locating and treating by a patient himself or herself of trigger points under the skin of his or her back, comprising an arcuate handle, and an extension on one end of the handle for engaging the skin on the patient's back and applying electrical stimulation thereto, wherein the handle is less than an arm's length in length, wherein the extension has a rounded point on its free end, wherein the extension is spade-shaped and has tapering straight edges merging in the rounded point.

2. A wand according to claim 1, wherein the spade-shaped extension has a comparably-shaped sponge on it.

3. A wand according to claim 2, wherein the comparably-shaped sponge has a pocket in it for being received on the extension.

4. A wand according to claim 1, wherein the arcuate handle is made of an electrically conductive material covered with a non-electrically-conductive material.

5. A wand according to claim 1, wherein the extension is made of an electrically-conductive material.

6. A wand according to claim 1, and a grip on the other end of the handle for facilitating moving the wand.

7. A wand according to claim 4, and a cable for electrically connecting the handle-electrically-conductive material through a rheostat and an on/off switch to a source of pulsed voltage.

8. An apparatus for locating and treating trigger points under the skin, comprising a source of pulsed voltage, and a wand having an arcuate handle and an extension on one end of the handle for enabling the patient himself or herself to engage the skin on his or her back, wherein the extension is spade-shaped and has on its free end tapering straight edges merging in a rounded point.

9. An apparatus according to claim 8, and the spade-shaped extension has a somewhat comparably-shaped sponge fixed to it.

10. An apparatus according to claim 9, wherein the extension is electrically conductive.

11. An apparatus according to claim 10, wherein the handle is formed with electrically-conductive material, and a cable connects the electrically-conductive material through a rheostat and an on/off switch to a source of pulsed voltage.

12. An apparatus according to claim 8, wherein the arcuate handle is less than an arm's length in length.

13. An apparatus according to claim 11, wherein the handle is covered with an electrically non-conductive material.

* * * * *